United States Patent [19]

Feng et al.

[11] Patent Number: 5,290,222
[45] Date of Patent: Mar. 1, 1994

[54] INJECTION PORT CONNECTOR WITH ROTATABLE LOCKING LUG

[76] Inventors: Jiyu Feng; Esther C. Feng, both of 201 S. 3rd Ave., #4, Arcadia, Calif. 91006

[21] Appl. No.: 776,440

[22] Filed: Oct. 15, 1991

[51] Int. Cl.$^5$ ............................................. A61M 37/00
[52] U.S. Cl. ..................... 604/86; 604/174; 604/283; 604/905
[58] Field of Search ..................... 604/83, 86–88, 604/174, 177, 179, 180, 201, 206, 244, 256, 283, 284, 905, 411; 285/361, 396

[56] References Cited

U.S. PATENT DOCUMENTS

| | | | |
|---|---|---|---|
| 3,986,508 | 10/1976 | Barrington | 604/905 |
| 4,219,912 | 9/1980 | Adams | 604/86 |
| 4,511,359 | 4/1985 | Vaillancourt | 604/411 |
| 4,752,292 | 6/1988 | Lopez et al. | 604/244 |
| 4,981,469 | 1/1991 | Whitehouse et al. | 604/86 |
| 5,071,404 | 12/1991 | Larkin et al. | 604/86 |
| 5,122,123 | 6/1992 | Vaillancourt | 604/86 |

FOREIGN PATENT DOCUMENTS

| | | | |
|---|---|---|---|
| 0319764 | 6/1989 | European Pat. Off. | 604/905 |
| 9116938 | 11/1991 | PCT Int'l Appl. | 604/283 |

*Primary Examiner*—John D. Yasko
*Assistant Examiner*—Anthony Gutowski
*Attorney, Agent, or Firm*—David O'Reilly

[57] ABSTRACT

An improved injection cap having a lug for locking the injection cap to a tubing connector. One embodiment has a lug integrally constructed on the injection cap. Another embodiment has a lug rotatably attached to the injection cap. Still another embodiment has a lug connected with a wing rotatably attached to the injection cap. An improved Y-injection site having a lug for locking a tubing connector on the Y-injection site. As before one embodiment has a lug integrally constructed on a side branch of a Y-injection site, while another embodiment has a lug rotatably attached to the side branch. The invention includes an improved tubing connector having a tubular needle sheath that is open at one end and closed by needle hub at another end. The sheath incorporates a catch mechanism to receive a lug-shaped attachment on an injection cap or a Y-injection site and ensure a secure connection. One variation has an open cut-out slit at the open end of needle sheath to receive and engage in a locking relation with a lug. In another embodiment a needle sheath has at least one straight open cut-out slit with two notches at the opening to receive and retain a lug. Still another embodiment has a second tubular sheath rotatably fitted on the outside of the first sheath. Open cut-out slits on the inner and outer sheaths can be in and out of alignment by rotation to receive and engage into a locking relation with a lug. A sheathed injection needle having a straight open cut-out slit on the needle sheath for accessing an injection site that has a lug-shaped attachment. A fluid container having an closing cap with a built-in injection site kept on the container with a retaining cap or it can engage the container directly.

13 Claims, 7 Drawing Sheets

INJECTION PORT CONNECTOR WITH ROTATABLE LOCKING LUG

FIELD OF THE INVENTION

The present invention relates to safety connectors for parenteral fluid administration systems, and more specifically to improved connections for injection caps, injection sites, tubing connectors, injection needles with a protective sheath, and containers with a built-in injection site.

BACKGROUND OF THE INVENTION

In recent years as the problem of tansmissible diseases, such as AIDS, escalating, the need for safe intravenous fluid administration systems, which can prevent health care personnel from accidental needle injuries, is strongly felt among health care providers and researchers. In practice there are three most common situations where intravenous fluid administration systems are used.

The first is where an open end of a catheter is introduced into a vein in a patient's arm, and the other end of the catheter is outside the patient and closed by an injection cap with a needle-penetrable self-sealing injection port. The injection cap is secured on the patient's skin by taping. Fluids can be withdrawn or supplied through a needle that penetrates the injection port. The needle is connected to a syringe or to one end of a tubing with a fluid source supplied at the other end. This set up is called a periphery line.

The second is where an open end of a catheter is introduced into a vein in a patient's arm, and the other end is outside the patient and connected to one end of a tubing with a primary fluid source continuously supplied at the other end. Along the tubing there are constructed a number of injection sites. The injection sites are usually in the form of a short side branches of hard tubes connected to the main tubing and closed by needle-penetrable self-sealing injection ports. The injection ports are called Y-injection sites. Additional fluids can be withdrawn or supplied through a needle that penetrates the injection port of one of the Y-injection site. The needle is connected to a syringe or to one end of a tubing with a secondary fluid source supplied at the other end.

The third is where an open end of a catheter with one or more lumens is inserted into a vein in a patient's chest and the catheter is sutured to the patient's skin. Each branch of the lumen, if there are more than one, is outside the patient and closed by an injection cap with a needle-penetrable self-sealing injection port. Fluids can be withdrawn or supplied through a needle that penetrates inside the injection port. The needle is connected to a syringe or to one end of a tubing with a fluid source supplied at another end. This set up is called a central line.

In the aforementioned and other situations, because needles are used to connect catheters and fluid supply sources, health care personnel who handle those fluid administration systems are exposed to the danger of contracting tansmissible diseases, such as AIDS, from accidental needle injuries. Another problem with the needle connection is that the needle and the injection cap must be taped together to ensure a good connection. Extra precautions must be taken in taping, since the connection can often get loose, on the other hand if the taping is too tight, it becomes very difficult to disconnect. There have been several previous attempts to develop safety devices in intravenous fluid administration systems with limited success.

One such tubing connector is disclosed in U.S. Pat. No. 4,964,855. It can lock with the side branch of a Y-injection site, but can not be used on central lines and periphery lines.

Another tubing connector is disclosed in U.S. Pat. No. 4,834,716. It can be fitted but can not be locked on a Y-injection site. Taping is still required to secure the connection. This connector can not be used on periphery lines.

A combination of an tubing connector and an injection cap is disclosed in U.S. Pat. No. 4,950,260. Since the locking arrangement prevents taping of the injection cap to a patient's skin, this set can not be used on periphery lines without an additional extension tubing.

Another combination of a tubing connector and an injection cap, Called Kleen-Needle System, is made by Tri-State Hospital Supply Corp. of Howell, MI 48843. The tubing connector can be locked onto the injection cap by matching screw threads on the outside of the injection cap and on the inside of the needle sheath of the tubing connector. After the injection cap being taped on a patient's skin it is difficult to make a locking engagement, so this set is inconvenient for use on periphery lines without an additional extension tubing.

Still another combination of a tubing connector and an injection cap is disclosed in U.S. Pat. No. 4,752,292. Since the locking mechanism on the tubing connector prevent the injection cap being taped on a patient, it can not be used on a periphery line without an additional extension tubing.

Baxter health care Corporation of Deerfield, IL 60015 has made a Needle-Less System including an injection cap and a tubing connector. On the tubing connector a sharp needle is replaced by a large diameter blunt plastic cannula. When forced into the injection port the plastic cannula makes a large puncture on the injection port. This puts a very high demand on the self-sealing property of the injection port. In practice the injection port may not work very well.

The safety devices so far, while they work under certain situations, all have some limitations on their applicability and some inconveniences in their usage. The additional extension tubing on the injection cap in some of the prior art, for example, not only increases the cost, it also requires extra steps of purging air from the tubing and taping the tubing on a patient. There exists a need for safety intravenous fluid administration systems which can be interchangeably used in different applications. Particularly there is a need for the combination of injection caps and tubing connectors which can be easily and reliably used on periphery lines.

It is one object of the invention to provide an improved safe injection cap that includes a locking lug for positively locking the connection with a tubing connector.

Another object of the present invention is to provide an improved safe injection cap that includes an attachment wing for securely fastening the injection cap to a patient.

Still another object of the present invention is to provide an improved safe Y-injection site that includes a locking lug for positively locking the connection with a tubing connector.

Yet another object of the invention is to provide an improved safe tubing connector that can be interchangeably used on the improved injection caps and Y-injection sites.

Yet another object of the invention is to provide an improved safe tubing connector that can be connected and disconnected with minimum manipulation.

Yet another object of the present invention is to provide an improved safe tubing connector for an injection site built on a container, an I.V. line, and the like to safely remove or supply fluids.

Yet another object of the present invention is to provide an improved safe injection needles with a protective sheath for an injection site built on a container, an I.V. line, and the like to safely remove or supply fluids.

Yet another object of the present invention is to provide an improved container with built-in injection site for a sheathed injection needle or a tubing connector to remove fluid from the container.

Yet another object of the present invention is to provide a combination of injection caps and tubing connectors which can be easily and reliably used on periphery lines.

Yet another object of the present invention is to provide a safe parenteral fluid administration system that including an improved injection cap, Y-injection site, tubing connector, sheathed injection needle and container with a built-in injection site, which can protect its user from inadvertent needle injuries in almost all common applications.

SUMMARY OF THE INVENTION

The purpose of the present invention is to provide a safe and secure locking connection for injection sites and tubing connectors that is easy to use and will not easily come apart. The invention includes the following.

A injection cap having attachment means for facilitating the attachment to a patient and a lug-shaped locking means for engaging with a corresponding locking device on a tubing connector.

In one embodiment, a section of the outer surface on an injection cap is provided for taping to a patient, and a lug-shaped locking means is integrally constructed on the outside of the injection cap.

In another embodiment, a section of the outer surface on an injection cap is provided for taping to a patient, and a lug-shaped locking means is rotatably attached to the injection cap.

In still another embodiment, a semi-flexible flat wing integrally formed with a lug-shaped locking means is provided for attachment to a patient, and said lug-shaped locking means and said wing are rotatably attached to an injection cap.

A Y-injection site having a lug-shaped locking means attached to each side tube, for engaging with a corresponding locking device on a tubing connector.

In one embodiment, a lug-shaped locking means is integrally constructed on each side tube.

In another embodiment, a lug-shaped locking means is rotatably attached to each side tube.

A connector for joining a tubing to injection caps and Y-injection sites having lug-shaped locking means thereon, the connector having a tubular needle sheath with a needle therein, said needle sheath having a catch means formed thereon, said catch means being constructed to corporate with said lug-shaped locking means on said injection caps and said Y-injection sites to form a locking relation therewith.

In one embodiment, the needle sheath has an open cut-out axial slit at its opening for receiving and forming a locking relation with said lug-shaped locking means.

In another embodiment, the needle sheath has at least one straight open cut-out axial slit with a pair of opposing notches at its opening for receiving and retaining said lug-shaped locking means inside said open slit.

In still another embodiment, the needle sheath has at least one straight open cut-out axial slit at its opening, and a second tubular outer sheath having an open cut-out slit at one of its open ends is rotatably fitted onto the outside of the first sheath. The open cut-out slits on the inner and the outer sheathes can be in and out of alignment by rotation to receive and engage into a locking relation with said lug-shaped locking means.

A sheathed injection needle for accessing injection caps and Y-injection sites with locking means having a straight open cut-out slit at the opening of the needle sheath. The sheathed injection needle can be fitted onto a syringe to remove fluid from or supply fluid to an injection site.

A fluid container for a sheathed injection needle or a tubing connector to remove fluid therefrom having an closing cap with a built-in injection site to seal its opening.

In one embodiment, a closing cap with a built-in injection site is retained on a container by a retaining cap.

In another embodiment, a closing cap with a built-in injection site engages the container directly to close the container.

The above and other novel features and advantages of the invention will be more fully understood from the following detailed description and the accompanying drawings where like reference numbers indicate like parts throughout.

DETAILED DESCRIPTION OF THE PREFERRED EMBODIMENTS

Figure 1:
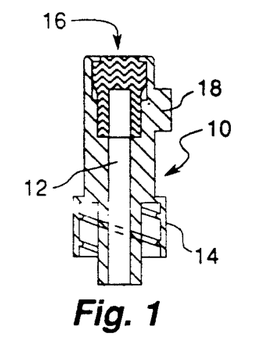
FIG. 1 is a sectional view of an injection cap with a built-in locking lug according to the invention.

An injection cap with a built-in locking lug according to the invention is shown in FIG. 1. The injection cap 10 has a generally cylindrical body of a medical grade plastic with a coaxial fluid passage 12. A luer lock 14 is provided at one end of the injection cap and an injection port 16 of the general structure shown in FIG. 9(d) closes the other end. On the outside of the injection cap body there is an integrally constructed locking lug 18. This injection cap can be used with the tubing connectors of FIGS. 10(a), 15, 17(c) and the sheathed needle of FIG. 19(a). It is simpler than the injection caps in FIGS. 3(d) and 5(c), and useful for central lines.

Figure 2:
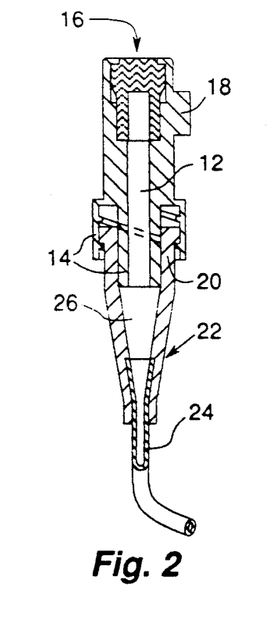
FIG. 2 is a sectional view of the injection cap with a built-in locking lug of FIG. 1 connected to a catheter.

FIG. 2 shows a sectional view of the injection cap with a built-in locking lug of FIG. 1 connected to a catheter. Luer lock 14 on the injection cap engages luer lock adapter 20 on catheter hub 22. Fluid passage 12 is in fluid communication with catheter 24 through fluid passage 26. In use, catheter 24 is inserted into a vein in a patient's chest by surgical procedures and secured on the patient's skin by suturing, and catheter hub 22 is outside the patient. The injection cap can be screwed onto catheter hub 22. Fluids can be supplied to or withdrawn from the patient's vein through injection port 16.

Figure 3A:
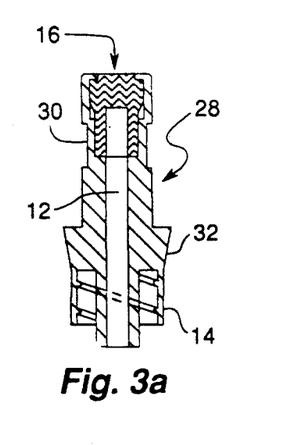
FIGS. 3(a) through 3(d) are sectional views of an injection cap with a floating rotatable locking lug according to the invention prior to and after assembly.
Figure 3B:
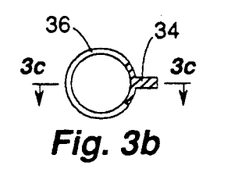
Figure 3C:
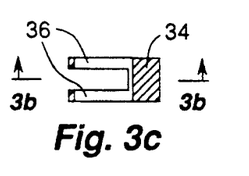
Figure 3D:
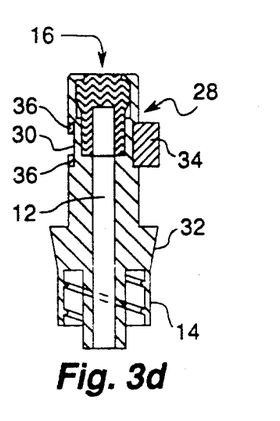

An injection cap with a floating rotatable locking lug according to the invention is shown in FIGS. 3(a) through 3(d). As shown FIG. 3(a) the injection cap 28 has a generally cylindrical body preferably of a medical grade plastic with a coaxial fluid passage 12. At one end of injection cap 28 is a luer lock 14, and an injection port 16 of the same general structure as shown in FIG.(d) closes the other end. An annular recess 30 is provided on the outside of the injection cap body. Adjacent to luer lock 14 and around the outside of the injection cap body there is a continuously and outwardly extended conically tapered surface 32. Surface 32 can be used to tape the injection cap securely on a patient. FIGS. 3(b) and 3(c) show a locking lug 34 with a band formed by cylindrical rings 36. Locking lug 34 is integrally connected to cylindrical rings 36. Locking lug 34 and rings 36 are of a semi-flexible plastic. An assembled injection cap with a floating rotatable locking lug is shown in FIG. 3(d). Rings 36 are first expanded to fit over the end of injection cap 28 then shrunk fit in annular recess 30 so that locking lug 34 can rotate freely relative to but can not be dislodged from the injection cap body. This injection cap can be used with the tubing connectors of FIGS. 10(a), 15, 17(c) and the sheathed injection needle of FIG. 19(a).

Figure 4:
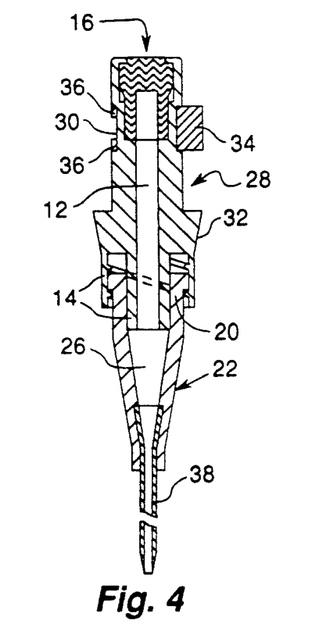
FIG. 4 is a sectional view of the injection cap with a floating rotatable locking lug of FIG. 3(d) connected to a catheter.

FIG. 4 shows a sectional view of the injection cap with a floating rotatable locking lug in FIG. 3(d) connected to a catheter. Luer lock 14 on the injection cap engages luer lock adapter 20 on catheter hub 22. Fluid passage 12 is in fluid communication with catheter 38 through fluid passage 26. In use, catheter 38 is introduced into a vein in a patient's arm by an introducer needle (not shown) and catheter hub 22 is outside the patient. Injection cap 28 can be screwed onto catheter hub 22 and locking lug 34 to point away from the patient's skin. Injection cap 28 can be secured to the patient's skin by taping to surface 32. Fluids can be supplied to or withdrawn from the patient's vein through injection port 16.

Figure 5A:
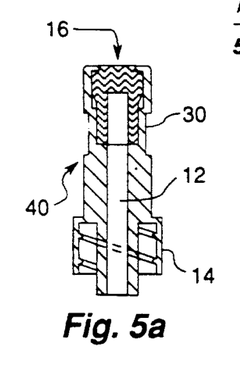
FIGS. 5(a) through 5(f) are sectional views of a winged injection cap of the present invention prior to and after assembly.

An winged injection cap of this invention is shown in FIGS. 5(a) through 5(f). As shown in FIG. 5(a) injection cap 40 has a generally cylindrical body preferably of a medical grade plastic with. coaxial fluid passage 12. At one end of injection cap body 40 is luer lock 14, and an injection port 16 of the general structure shown in FIGS. 9(a) through 9(d) closes the other end. On the outside of injection cap body 40 there is an annular recess 30.

Figure 5B:
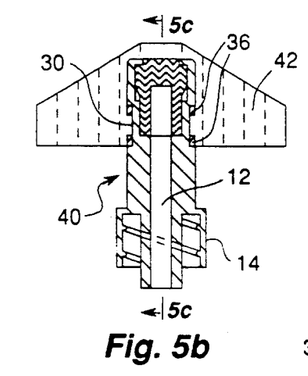
Figure 5C:
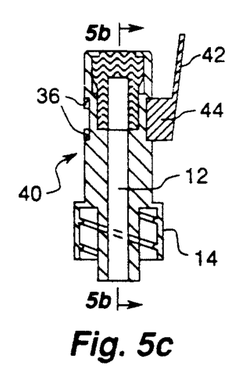
Figure 5D:
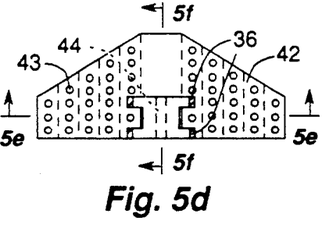
Figure 5E:
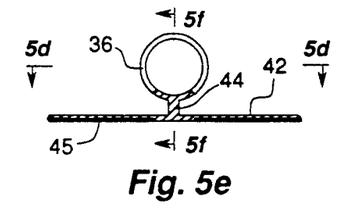
Figure 5F:
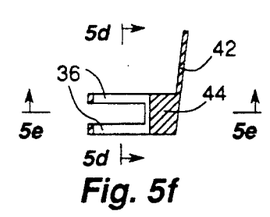

FIG. 5(d) to 5(f) show a wing-shaped appendage with rings. A flat wing-shaped appendage 42 is connected to circular rings 36 by a lug-shaped connection locking member 44. Wing-shaped appendage 42 and rings 36 are of a semi-flexible plastic. Wing-shaped appendage 42 can have a plurality of holes 43 as shown in FIG. 5(d). That will allow air to pass through if desired. Also an adhesive 45 can be added beneath win-shaped appendage 42 as shown in FIG. 5(e) to fasten the injection cap to a patient's skin. The assembled winged injection cap is shown in FIGS. 5(b) and 5(c). Rings 36 are first expanded to fit over the end of injection cap 40 then shrunk fit into circular recess 30 such that wing-shaped appendage 42 rotates freely relative to but can not be removed from the injection cap body. The winged injection cap can be used with the tubing connectors of FIGS. 10(a), 15, 17(c) and the sheathed injection needle of FIG. 19(a).

Figure 6:
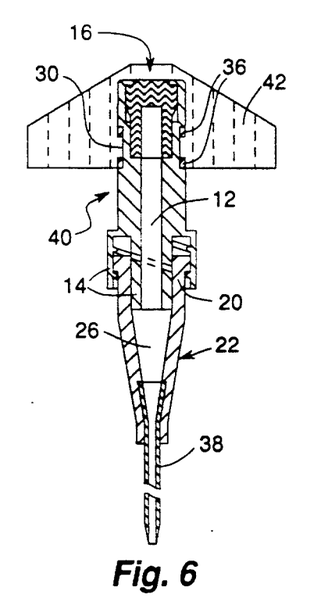
FIG. 6 is a sectional view of the winged injection cap in FIG. 5(b) connected to a catheter.

FIG. 6 is a sectional view of the winged injection cap of FIG. 5(b) connected to a catheter. Luer lock 14 on injection cap 40 engages luer lock adapter 20 on catheter hub 22. Fluid passage 12 is in fluid connection with catheter 38 through fluid passage 26. In use, catheter 38 is introduced into a vein in a patient's arm by a introducer needle (not shown) and catheter hub 22 is outside the patient. Since wing-shaped appendage 42 can rotate freely relative to the injection cap body, the winged injection cap can easily be screwed onto catheter hub 22. The function of wing-shaped appendage 42 is to secure the winged injection cap on the patient by taping or other means. Fluids can be supplied to or withdrawn from the patient's vein through injection port 16.

Figures 7A, 7B:
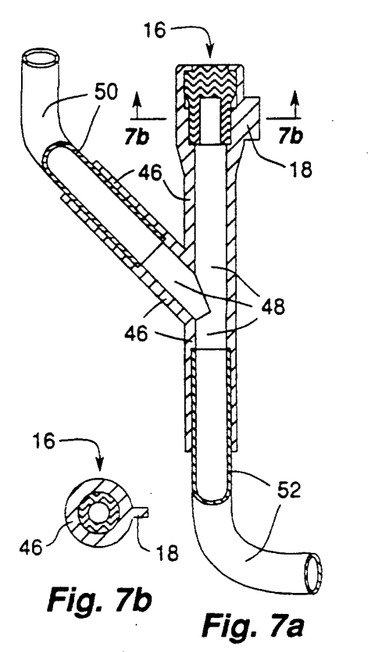
FIGS. 7(a) and 7(b) are sectional views-of a Y-injection site with a built-in locking lug according to the invention.

A Y-injection site with a built-in locking lug of this invention is shown in FIGS. 7(a) and 7(b). The basic structure is three branches of integrally molded tubes 46 of a preferably transparent medical grade plastic. The three branches of tubes 46 are in fluid communication with one another through fluid passages 48. The first branch is connected to tubing 50 that can be supplied with a fluid, the second branch is connected to tubing 52 that leads to a patient, and the third branch is closed by injection port 16 with the structure similar to that of FIG. 9(d). On the outside of the third branched tube there is an integrally constructed locking lug 18. Additional fluids can be supplied to or withdrawn from the primary I.V. line through injection port 16 at the end of the third branched tube. This Y-injection site can be used with the tubing connectors of FIGS. 10(a), 15, 17(c), and the sheathed injection needle of FIG. 15(a).

Figure 8:
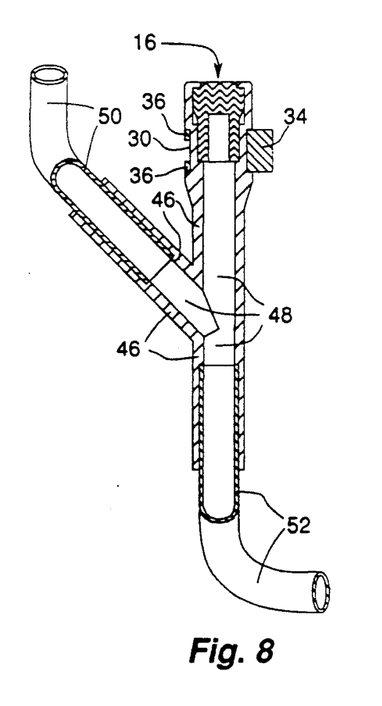
FIG. 8 is a sectional view of a Y-injection site with a floating, rotatable locking lug according to the invention.

A Y-injection site with a rotatable locking lug according to another embodiment of the invention is shown in the sectional view of FIG. 8. The basic structure is three branches of integrally molded tubes 46 of a preferably transparent medical grade plastic. The three branches of tubes 46 are in fluid communication with one another through fluid passages 48. The first branch is connected to tubing 50 that can be supplied with a fluid source, the second branch is connected to tubing 52 that leads to a patient, and the third branch is closed by injection port 16 with a structure similar to that shown in FIG. 9(d). On the outside of the third branched tube there is an annular recess 30. Locking lug 34 has a band formed by rings 36 shrunk fitted into annular recess 30 so it can be rotated relative to but can not be dislodged from the Y-injection site body. Additional fluids can be supplied to or withdrawn from the primary I.V. line through injection port 16 at the end of the third branched tube. Similarly this Y-injection site can be used with the tubing connectors of FIGS. 10(a), 15, 17(c), and the sheathed injection needle of FIG. 19(a).

Figure 9A:
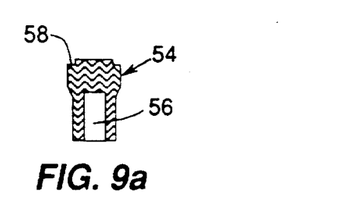
FIGS. 9(a) through 9(d) are sectional views of an injection port of this invention prior to and after assembly.
Figure 9B:
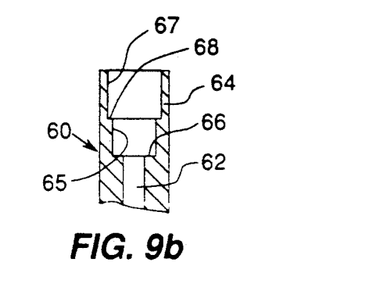
Figures 9C, 9D, 11A:
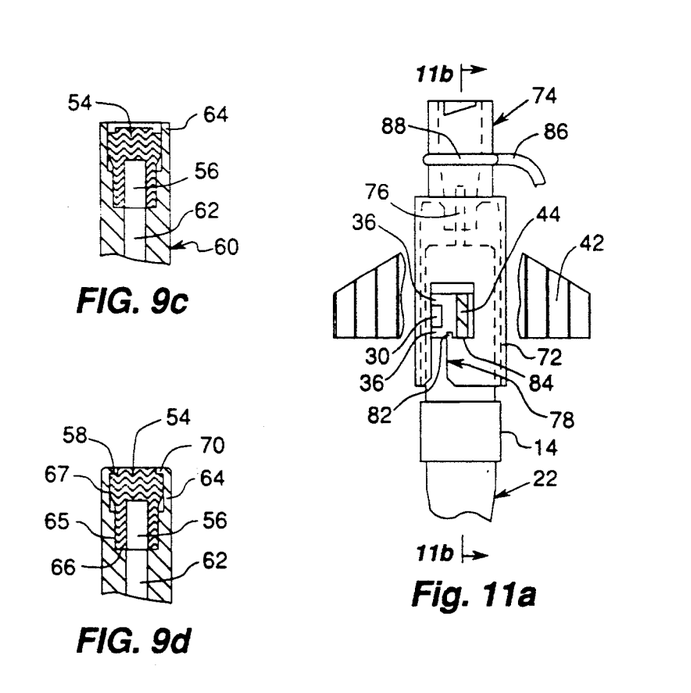
FIGS. 11(a) and 11(b) are sectional views of the tubing connector of FIG. 10(a) connected to and locked with a winged injection cap as shown in/ FIGS. 5(b) and 5(c).

An injection site according to the invention is shown in sectional views in FIGS. 9(a) through 9(d) prior to and after assembly. As shown in FIG. 9(a) a sealing plug 54 of an elastomeric material is of generally cylindrical shape with a smaller cross-section at one end and a larger cross-section at another end. A coaxial cutout hole 56 open at the smaller end is terminated inside the sealing plug 54. An annular indentation 58 is formed at the edge of the larger end of sealing plug 54. A tubular cylindrical injection site body 60 of preferably, medical grade plastic has a coaxial fluid passage 62. Fluid passage 62 opens to sealing plug housing 64 which consists of first annular recess 65 and second annular recess 67 that forms first annular shoulder 66 and second annular shoulder 68 as shown in FIG. 9(b). The larger cylindrical section of sealing plug 54 has a tight interference fit with the annular recess 67. Sealing plug 54 is pressed into sealing plug housing 64 and the end of sealing plug housing 64 extends beyond the end of sealing plug 52 as shown in FIG. 9(c). The end portion of sealing plug housing 64 is then bent inwardly to form annular lip 70 by thermal plastic methods or other means as shown in FIG. 9(d). Annular lip 70 fits onto annular indentation 58 at the end of sealing plug 54 and squeezes sealing plug tightly against first annular shoulder 66. This makes the sealing plug 54 expand against the annular recess 65 and annular recess 67. By axial and radial expansion sealing plug 54 forms a fluid-tight self-sealing injection port at the end of the injection site. The general structure of this injection site has been used on variety of devices in this invention.

Figure 10A:
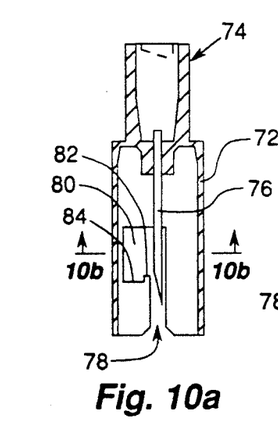
FIG. 10(a) and 10(b) are sectional views of one embodiment of the tubing connector according to the present invention.
Figure 10B:
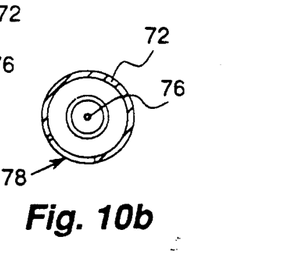

A tubing connector of this invention is shown in sectional views in FIGS. 10(a) and 10(b). The tubing connector is preferably of a transparent medical grade plastic and has a cylindrical tubular protective needle sheath 72. Needle sheath 72 is closed at one end by an integrally constructed needle hub 74 with a luer lock adapter. A needle 76 coaxially disposed inside protective needle sheath 72 is integrally constructed on and in fluid communication with needle hub 74. The other end of protective needle sheath 72 is open and extends beyond the sharp point of needle 76. At the open end on protective needle sheath 72 a locking slit 78 is formed by a narrow straight opening cut-out area joined by a wider rectangular offset cutout area 80 having a notch 82 forming a locking catch 84.

Figure 11B:
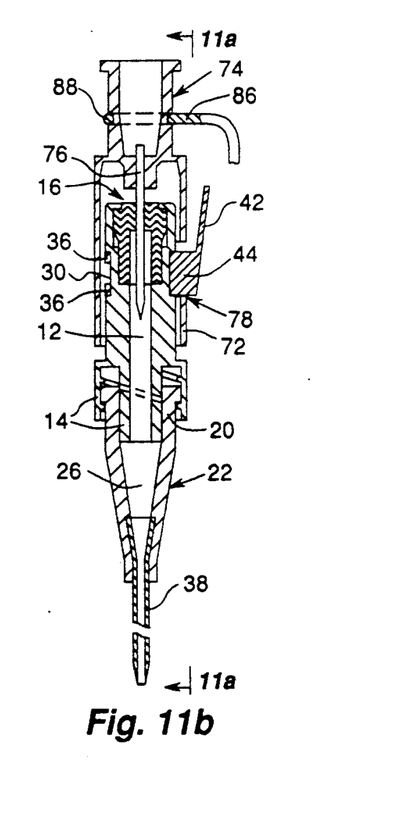

FIGS. 11(a) and 11(b) show in detail the locking relation between the winged injection cap of FIGS. 5(b) and 5(c) and the tubing connector of FIG. 10(a). In FIG. 11(a) part of wing-shaped appendage 42 is cut away to expose the locking arrangement. The opening of locking slit 78 is first aligned with lug-shaped connection locking member 44, and the tubing connector of FIG. 10(a) is pushed onto winged injection cap of FIGS. 5(b) and 5(c) until locking member 44 reaches the end of locking slit 78. At the same time needle 76 penetrates inside injection port 16 on injection cap 40. The tubing connector of FIG. 10(a) is then rotated clockwise relative to the winged injection cap until locking member 44 reaches the far side of offset 80 of the locking slit 78. Finally the tubing connector of FIG. 10(a) is pulled back (e.e. actually away) to let locking member 44 seat into a locking position in locking slit 78. Catch 84 prevents locking member 44 from being accidentally displaced out of locking slit 78 avoiding unintended disruptions of I.V. lines. The tubing connector of FIG. 10(a) can be removed from the winged injection cap by reversing the above procedure.

FIG. 11(b) is another sectional view of the tubing connector of FIG. 10(a) in a locking relation with winged injection cap of FIG. 5(b) and 5(c). Fluids can be supplied from a source through a tubing (not shown) connected to the luer lock adapter on needle hub 74, and through needle 76 and catheter 38 into a patient's vein. The tubing connector shown in FIG. 10(a) can also be fitted onto a syringe to supply fluid to or withdrawn fluid from the winged injection cap without locking with it. This setup can be used on periphery lines and central lines.

Figure 12:
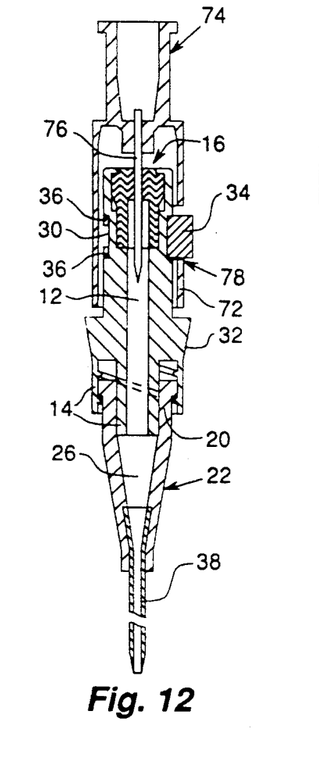
FIG. 12 is a sectional view of the injection cap with a floating rotatable locking lug of FIG. 3(d) connected to and locked with the tubing connector of FIG. 10(a).

FIG. 12 is a sectional view, of the injection cap with a floating rotatable lug of FIG. 3(d) in locking relation with the tubing connector of FIG. 10(a). The locking procedure is similar to that shown in FIG. 11(a) and 11(b). Fluids can be supplied from a source through a tubing (not shown) connected to luer lock adapter 74 then through needle 76 and catheter 38 into a patient's vein. The tubing connector of FIG. 10(a) can also be fitted onto a syringe to supply fluid to or withdrawn fluid from the injection cap in FIG. 3(d) without being locked to it. This setup can be used on periphery lines and central lines.

Figures 13, 15:
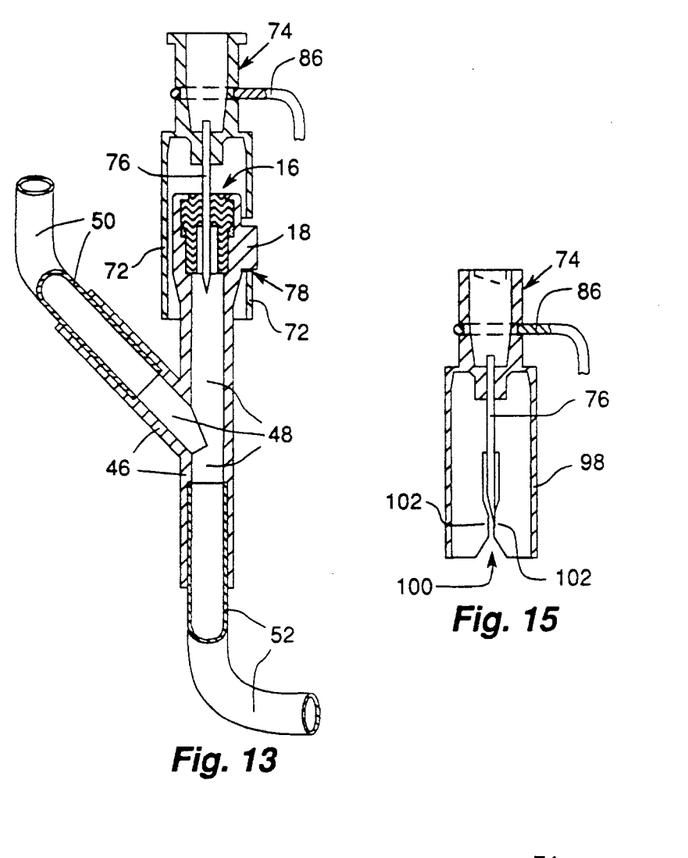
FIG. 13 is a sectional view of the injection site with a built-in locking lug of FIG. 7(a) connected to and locked with the tubing connector of FIG. 10(a).
FIG. 15 is a sectional view of another embodiment of the tubing connector according to the present invention.
Figure 13A:
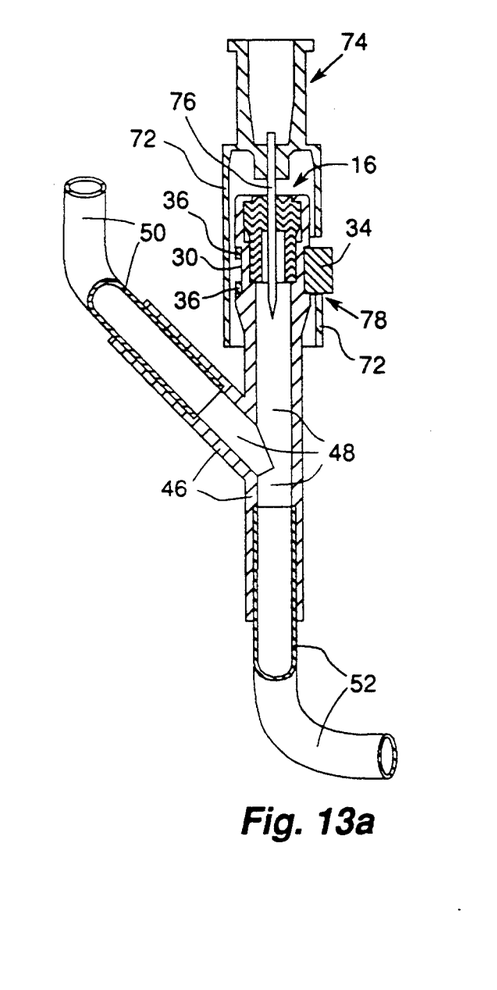

FIG. 13 shows the Y-injection site of FIG. 7(a) connected to the tubing connector of FIG. 10(a). The connection is made by following a procedure similar to the connection/of the tubing connector to the winged injection cap of FIGS. 5(b) and 5(c). The opening of locking slit 78 is first aligned with locking lug 18, and the tubing connector of FIG. 10(a) is pushed onto the Y-injection site until locking lug 18 reaches the end of locking slit 78, at the same time needle 76 penetrates inside injection port 16. The tubing connector of FIG. 10(a) is then rotated clockwise relative to the Y-injection site until locking lug 18 reaches the far side of offset 80 in locking slit 78. Finally the tubing connector is pulled back to let locking lug 18 seat into its locking position secured by catch 84 in locking slit 78. The tubing connector can be removed from the Y-injection site by reversing the above procedure. Locking lug 18 thus ensures a firm connection of a secondary I.V. line (not shown), through needle hub 74 of the tubing connector to the Y-injection site with a built-in locking lug, and therefore prevents unintended disruptions of the I.V.. line. The tubing connector of FIG. 10(a) can also be fitted onto a syringe to supply fluid to or withdrawn fluid from the Y-injection site without being locked to it.

Figure 14A:
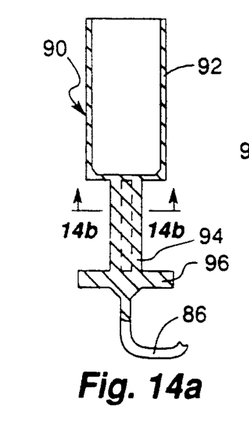
FIGS. 14(a) through 14(c) are sectional views of a protective cap for the tubing connector of FIG. 10(a) prior to and after being mated with the tubing connector.
Figure 14B:
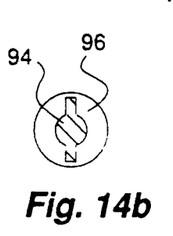
Figures 14C, 16:
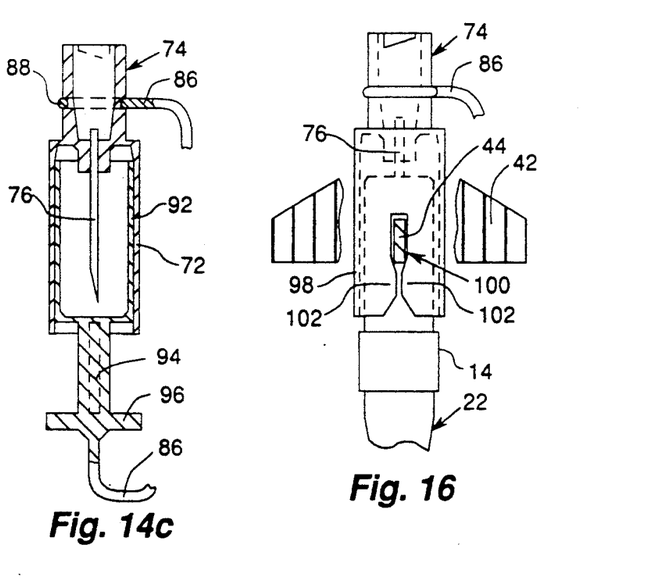
FIG. 16 is a sectional view of the tubing connector in FIG. 15 connected to the winged injection cap of FIGS. 5(b) and 5(c).

A protective cap for tubing connector of FIG. 10(a) is shown in sectional views of FIGS. 14(a) through 14(c). Protective cap 90 has cylindrical tubular body 92 opening at one end and closed by an elongate handle 94 followed with an end plate 96. FIG. 14(c) shows the tubing connector of FIG. 10(a) mated with protective cap 90 of FIG. 14(a). Protective cap body 92 can fit snugly into needle sheath 72. Toward the closed end of the needle sheath 72 the inside wall has a gradually decreasing diameter so that it can hold cap body 92 by friction, and the cap can also be easily removed with a moderate pulling force. One end of connection string 86 is attached to end plate 96 and the other end is formed into a ring 88 which fits into a circular recess on the outside of needle hub 74. Connection string 86 prevents protective cap 90 from being lost when it is not mated with the tubing connector of FIG. 10(a). Protective cap 88 is useful when the tubing connector is intended for repeated use.

Another embodiment of the tubing connector of this invention is shown in sectional view in FIG. 15. The tubing connector is preferably of a transparent medical grade plastic and has a cylindrical tubular protective needle sheath 98. Needle sheath 98 is closed at one end by an integrally constructed needle hub 74 with a luer lock adapter. A needle 76 coaxially disposed inside protective needle sheath 98 is integrally constructed on and in fluid communication with needle hub 74. The other end of protective needle sheath 98 is open and extends beyond the sharp point of needle 76. At the open end on protective needle sheath 98 an open slit 100 is formed by a straight opening cut-out area with two opposing notches 102 at its opening, two notches 102 defines a narrow entry way into the wider inside of open slit 100

FIG. 16 shows the connecting relation; between the winged injection cap of FIG. 5(b) and 5(c) the tubing connector of FIG. 15. Part of wing-shaped appendage 42 is cut away to expose the connection. The opening of slit 100 is first aligned with lugshaped connection locking member 44, and the tubing connector of FIG. 15 is pushed onto the winged injection cap. The entry way defined by two notches 102 at the opening of open slit 100 has a width less than the width of locking member 44. Needle sheath 98 deforms as locking member 44 passes the entry way defined by two notches 102 into the wider inside of open slit 100. Locking member 44 is retained inside open slit 100 by two notches 102. The tubing connector in FIG. 15 can be pulled off the winged injection cap by a moderate force. The tubing connector shown in FIG. 15 can also be fitted onto a syringe to supply fluid to or withdrawn fluid from the winged injection cap. This setup can be used on periphery lines and central lines. The tubing connector in FIG. 15 can also be used on other injection caps and Y-injection sites of this invention.

Figure 17A:
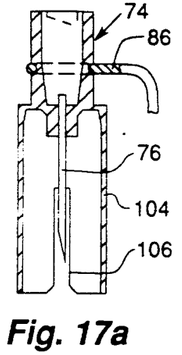
FIGS. 17(a) through 17(d) are sectional views of still embodiment of the tubing connector according to this invention prior to and after assembly.
Figure 17B:
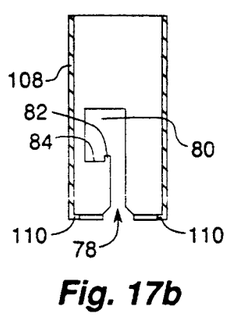

Still another embodiment of the tubing connector of this invention is shown in FIGS. 17(a) through 17(d) prior to and after assembly. The first part of the tubing connector is a needle with a sheath as shown in FIG. 17(a). A cylindrical tubular needle sheath 104 of a preferably transparent medical grade plastic is closed at one end by an integrally constructed needle hub 74 with a luer lock adapter. Needle 76 is coaxially disposed inside needle sheath 104 and is integrally constructed on and in fluid communication with needle hub 74. The other end of needle sheath 104 is open and extends beyond the sharp point of needle 76. At the open end on needle sheath 104 there is an open slit 106 which is a straight opening cut-out area. The second part of this tubing connector is a second sheath 108 as shown in FIG. 17(b). Cylindrical tubular sheath 108 of a preferably transparent medical grade plastic is open at both ends. The end portion of the first end of sheath 108 is bent inwardly to form an annular lip 110 perpendicular to the wall of needle sheath 108. At the first end of needle sheath 108 there is a locking slit 78 which is formed by a narrow straight opening cut-out area joined by a wider rectangular offset cutout area 80 with a notch 82 and catch 84. The second end opposite lip 110 of sheath 108 is straight before assembly.

Figure 17C:
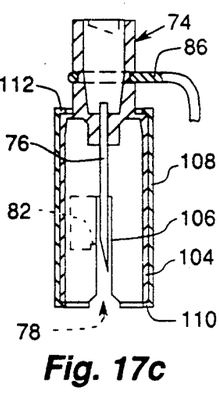
Figure 17D:
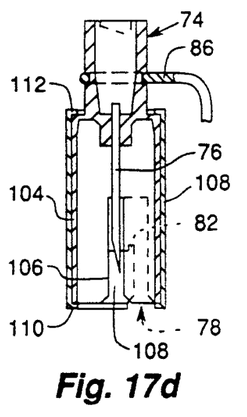

FIG. 17(c) is a sectional view of the assembled double sheathed tubing connector. Outer sheath 108 snugly fits onto the outside of inner sheath 104 and the second end of outer sheath 108 extends beyond the inner sheath 104 toward needle hub 74. The second end of outer sheath 108 is bent inwardly to form a second annular lip 112 thermal elastically or by other means. Annular lips 110, 112 at both ends of the outer sheath 108 are formed so that outer sheath 108 can rotate freely relative to but can not be removed in either direction axially from inner sheath 104. In FIG. 17(c) straight open slit 106 on the inner sheath 104 is aligned with the opening of locking slit 78 on the outer sheath 108. In FIG. 17(d) the opening of locking slit 78 on outer sheath 108 is rotated out of alignment with straight open slit 106 on inner sheath 104.

Figure 18A:
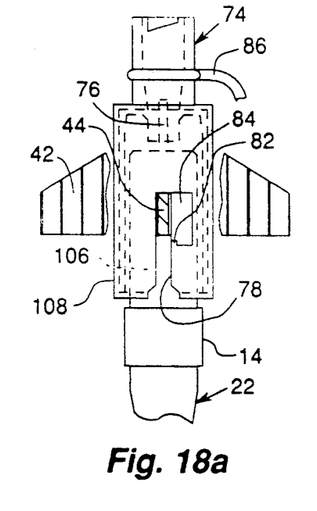
FIGS. 18(a) and 18(b) are sectional views of the double sheathed tubing connector of FIGS. 17(c) and 17(d) prior to and after locking with the winged injection cap of FIGS. 5(b) and 5(c).
Figures 18B, 19A:
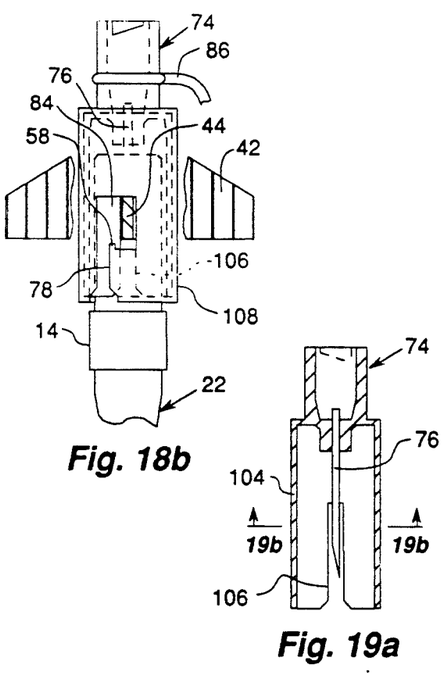
FIGS. 19(a) and 19(b) are sectional views of a sheathed injection needle according to the invention.

FIGS. 18(a) and 18(b) show in detail the locking relation between the winged injection cap of FIGS. 5(b) and 5(c) and the tubing connector of FIG. 17(c) and 17(d). Part of wing 42 is cut away to expose the locking arrangement. In FIG. 18(a) the opening of locking slit 78 on outer sheath 108 is first aligned with straight open slit 106 on inner sheath 104. Connection locking member 44 is then aligned with straight open slit 106 and the double sheathed tubing connector is pushed onto the winged injection cap to allow connection locking member 44 to reach the end of straight open slit 106 on inner sheath 104. Finally outer sheath 108 is rotated to cause the opening of locking slit 78 to be out of alignment with straight open slit 106 on inner sheath 104 as shown in FIG. 18(b). Connection locking member 44 is locked inside straight open slit 106 and the wider rectangular offset area 80 of locking slit 78( Therefore unintended disruptions of the I.V. line can be, prevented. The double sheathed tubing connector of FIGS. 17(c) and 17(d) can be removed from the winged injection cap of FIGS. 5(b) and 5(c) by reversing the above procedure. Similarly this tubing connector can be used on the Y-injection sites in FIGS. 7(a) and 8 and the injection caps of FIGS. 1 and 3(d)

Figure 19B:
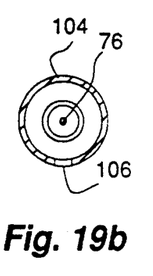

A sheathed injection needle of the invention is shown in FIGS. 19(a) and 19(b). Cylindrical tubular needle sheath 104 of a preferably transparent medical grade plastic is closed at one end by an integrally constructed needle hub 74 with a luer lock adapter. Needle 76 coaxially disposed inside needle sheath 104 is integrally constructed on and in fluid communication with needle hub 74. The other end of needle sheath 104 is open and extends beyond the sharp point of the needle 76. At the open end of the needle sheath 104 there is an open slit 106 which is a straight opening cut-out area. This sheathed injection needle is combined with a syringe to supply fluid to or withdrawn fluid from injection caps and Y-injection sites of this invention. To use it on the Y-injection site in FIG. 7, for example, the luer lock adapter on the needle hub 74 is fitted onto the luer fitting on a syringe (not shown). Open slit 106 is then aligned with locking lug 18 and the needle-syringe assembly is pushed forward to allow needle 76 to penetrate injection port 16. Similarly the sheathed needle of FIG. 19(a) can be used on another Y-injection site shown in FIG. 8, the injection caps of FIG. 1, 3(d) and 5(c), and the vials with built-in injection sites shown in FIGS. 20 and 21, as well as described in greater detail hereinafter.

Figures 20A, 20B, 20C:
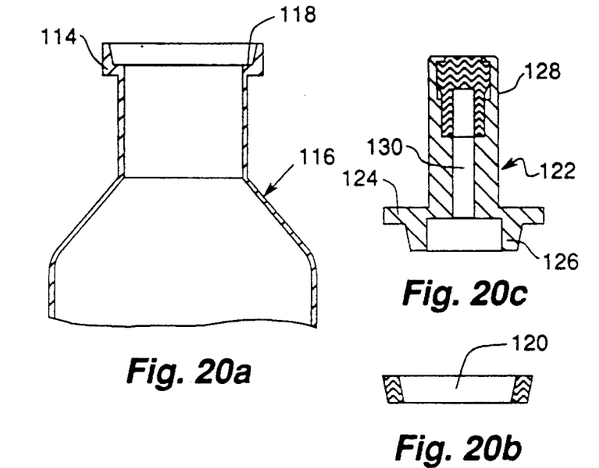
FIGS. 20(a) through 20(e) are sectional views of the embodiment of a vial with a built-in injection site according to the invention prior to and after assembly.
Figure 20D:
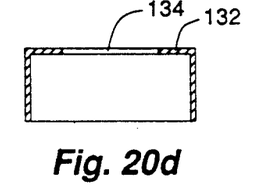
Figure 20E:
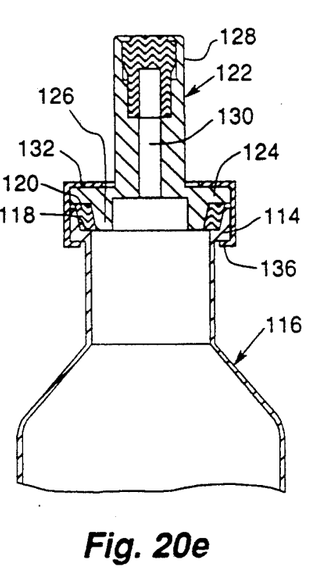

One embodiment of the vial with a built-in injection site according to the invention is shown in FIGS. 20(a) through 20(e) prior to and after assembly. An annular lip 114 is provided at the opening of vial 116 on the outside and an annular shoulder 118 on the inside as shown in FIG. 20(a). O-ring 120 having a parallelogram cross-sectional shape (i.e. tapered) is of an elastomeric material as shown in FIG. 20(b). O-ring 120 fits into annular shoulder 118 at the opening of vial 116. FIG. 20(c) shows a closing cap 122 preferably of a medical grade plastic with a built-in injection site for vial 116. Closing cap 122 has a circular plate 124 with an annular tapered ring 126 integrally constructed on its one end and an injection site 128 of the same general structure like that shown in FIG. 9(d) on its other end. Fluid passage 130 opens on the first side of circular plate 124. Annular tapered ring 126 fits inside tapered O-ring 120. A retaining cap 132 with a cut-out hole 134 through its top is shown in FIG. 20(d). FIG. 20(e) shows the assembled vial with a built-in injection site. Annular ring 126 fits tightly inside O-ring 120 with circular plate 124 and annular tapered ring 124 pressing O-ring 120 which seats tightly in annular shoulder 118 to form a fluid-tight closure for vial 116. Injection site 128 passes through cut-out hole 134 on the top of retaining cap 132. The opening of retaining cap 132 extends beyond annular lip 114 and the end portion of retaining cap 132 is bent inwardly to form annular lip 136. The flange at the top of retaining cap 132 and annular lip 136 hold firmly to circular plate 124 on closing cap 122 and annular lip 114 on vial 116 so as to maintain the assembly. Injection site 128 on closing cap 122 allows a syringe connected to the sheathed injection needle in FIG. 19(a) to withdraw fluid from vial 116 without an extra vial adapter for injection into an I.V. line.

Figures 21A, 21B, 21C:
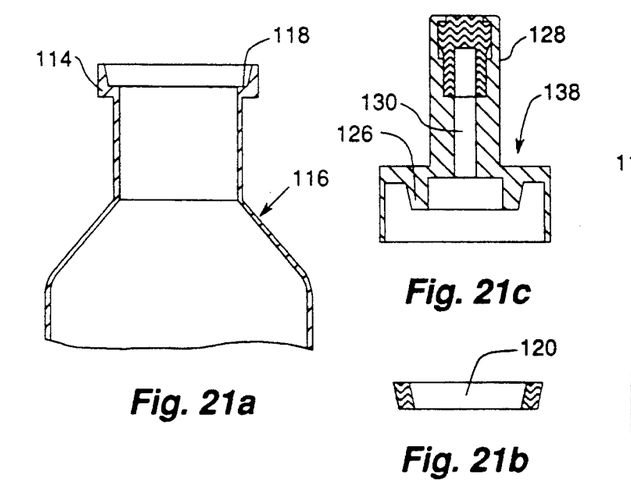
FIGS. 21(a) through 21(d) are sectional views of another embodiment of a vial with built-in injection site according to the invention prior to and after assembly.
Figure 21D:
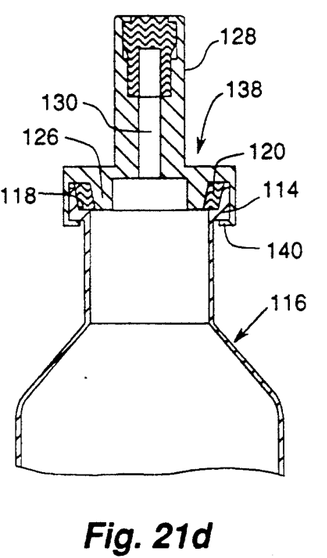

Another embodiment of the vial with a built-in injection site according to the invention is shown in FIGS. 21(a) through 21(d) prior to and after assembly. Vial 114 has annular lip 116 on the outside at the open end and annular shoulder 118 on the inside as shown in FIG. 21(a). O-ring 120 having a parallelogram cross-section tapered shape is of an elastomeric material as shown in FIG. 21(b). O-ring 120 fits into annular shoulder 118 at the opening of vial 114. FIG. 21(c) shows a closing cap 138 preferably of a medical grade plastic with a built-in injection site for vial 116. Closing cap 138 has tapered annular ring 126 integrally constructed on its inside one end and an injection site 128 of the same general structure like that shown in FIG. 9(d) on the other end. Fluid passage 130 opens to the inside of closing cap 138. Annular ring 126 can fit inside O-ring 120. FIG. 21(d) shows the assembled vial with a built-in injection site. Annular ring 120 fits tightly inside O-ring 120, and the inside end of closing cap 138 and annular ring 126 press O-ring 120 to seat tightly onto annular shoulder 118 to form a fluid-tight closure to vial 116. The opening of closing cap 138 extends beyond the annular lip 114, and the end portion of closing cap 138 is bent inwardly to form annular lip 140. Annular lip 140 holds firmly onto annular lip 114 on vial 116 so as to maintain the assembly. Injection site 128 on closing cap 138 allows a syringe connected to the sheathed injection needle of FIG. 19(a) to withdraw fluid from vial 116 without an extra vial adapter for injection into an I.V. line.

From the foregoing description, it can be appreciated that the safety parenteral fluid administration systems of this invention have the following advantages. The combination of the injection caps and tubing connectors of this invention can be used on periphery lines and central lines. The tubing connector can be interchangeable used on the injection caps and the Y-injection sites of this invention, and it gives a more secure and more sterile connection without the extra steps of taping. The vials with a built-in injection site allow the sheathed injection needle to withdraw fluid without the extra step and cost of using a vial adapter. The sheathed injection needle can be interchangeably used on the injection caps, the Y-injection sites and the containers with a built-in injection site according to the invention. The combined safety system of the injection caps, Y-injection sites, tubing connectors, sheathed injection needle and containers with a built-in injection site according to the invention covers all common applications of intravenous fluid administration. So the safety parenteral fluid administration system of this invention virtually eliminates the possibility of needle injuries to health care personnel. Additionally, since the devices in this invention are simple to make and can be interchangeably used, the cost can be reduced by using the safety system connectors of the invention.

This invention is not to be limited by the embodiments shown in the drawings and described in the description but only in accordance with the scope of the appended claims.

What is claimed is:

1. An injection port connector comprising: a tubular body having a coaxial fluid passage therethrough from a distal port to a proximal port, said proximal port being closed by a fluid-tight self-sealing means to form an injection port, said injection port being in fluid connection with said distal port through said fluid passage; an annular recess around the outside of said tubular body adjacent said injection port, a lug-shaped locking means being integrally formed with a band, said band being deformable to fit into said recess on the outside of said tubular body; whereby said lug-shaped locking means is rotatable relative to but not removable from said tubular body.

2. The injection port connector according to claim 1, wherein said distal port has a luer lock integrally constructed thereon.

3. The injection port connector according to claim 2, wherein an outwardly projecting short surface section is provided on the outer surface of said luer lock for facilitating attachment of said connector to a patient.

4. The injection port connector according to claim 3, wherein said injection port comprises; a first and a second coaxial recess forming a first annular shoulder and a second annular shoulder at said proximal port, said first coaxial recess being larger than the fluid passage, and said second coaxial recess following said first coaxial recess and being larger than said first coaxial recess; and, a resilient elastomeric sealing plug constructed to tightly fit said proximal port, said sealing plug being formed with a first cylindrical section joined by a second larger cylindrical section, said first cylindrical section having a smaller cross-section than said second cylindrical section; a coaxial cylindrical blind hole opening in said first cylindrical section, and an annular indentation being formed around the periphery of the end of said second cylindrical section; said sealing plug being pressed in said proximal port with said larger cylindrical section having a tight fit with said second coaxial recess, the end portion of said proximal port being bent inwardly to form an annular lip, said annular lip fitting into said annular indentation of said sealing plug, the end of said first cylindrical section being pressed tightly against said first annular shoulder in said proximal port, said first cylindrical section being caused to expand radially against said first coaxial recess; whereby said sealing plug forms a fluid-tight self-sealing injection port by axial and radial expansion.

5. The injection port connector according to claim 1, wherein said distal port is integrally connected to and in fluid connection with a plurality of tubes, one of said tubes begin a fluid outlet and at least one of remaining tubes being a fluid inlet.

6. The injection port connector according to claim 5, wherein said injection port comprises; a first and a second coaxial recess forming a first annular shoulder and a second annular shoulder at said proximal port, said first coaxial recess being larger than the fluid passage, and said second coaxial recess following said first coaxial recess and being larger than said first coaxial recess; and, a resilient elastomeric sealing plug constructed to tightly fit said proximal port, said sealing plug being formed with a first cylindrical section joined by a second larger cylindrical section, said first cylindrical section having a smaller cross-section than said second cylindrical section; a coaxial cylindrical blind hole opening in said first cylindrical section, and an annular indentation being formed around the periphery of the end of said second cylindrical section; said sealing plug being pressed in said proximal port with said larger cylindrical section having a tight fit with said second coaxial recess, the end portion of said proximal port being bent inwardly to form an annular lip, said annular lip fitting into said annular indentation of said sealing plug, the end of said first cylindrical section being pressed tightly against said first annular shoulder in said proximal port, said first cylindrical section being caused to expand radially against said first coaxial recess; whereby said sealing plug forms a fluid-tight self-sealing injection port by axial and radial expansion.

7. An injection port connector according to claim 1 including;

a second connector having a cylindrical tubular housing with an open and a closed port, a needle hub with a luer lock adapter being integrally constructed don said closed port, a needle coaxially disposed in said tubular housing being integrally constructed on and in fluid communication with said needle hub, the opening of the open port extending beyond the sharp point of said needle, an open axial slit being formed at said open port, said open slit having a first narrow straight opening cut-out area joined by a second wider generally rectangular offset cut-out area with a notch; said injection port and tubular body of said first connector being receivable in said open port of said second connector to permit said needle penetrating said injection port and said needle hub of said second connector establishing fluid connection to said distal port of said first connector, said lug-shaped locking means of said first connector being receivable in said open slit of said second connector to form a releasable locking relation therewith and secure a mutual connection of said two connectors.

8. The connector assembly according to claim 7, wherein said distal port of said first connector is integrally connected to a luer lock.

9. The connector assembly according to claim 8, wherein an outwardly projecting short surface section is provided on the outer surface of said luer lock for facilitating attachment of said first connector to a patient.

10. The connector assembly according to claim 9, wherein said injection port on said first connector comprises; a first and a second coaxial recess forming a first annular shoulder and a second annular shoulder at said proximal port, said first coaxial recess being larger than the fluid passage, and said second coaxial recess following said first coaxial recess and being larger than said first coaxial recess; and, a resilient elastomeric sealing plug constructed to tightly fit said proximal port, said sealing plug being formed with a first cylindrical section joined by a second larger cylindrical section, said first cylindrical section having a smaller cross-section than said second cylindrical section; a coaxial cylindrical blind hole opening in said first cylindrical section, and an annular indentation being formed around the periphery of the end of said second cylindrical section; said sealing plug being pressed in said proximal port with said larger cylindrical section having a tight fit with said second coaxial recess, the end portion of said proximal port being bent inwardly to form an annular lip, said annular lip fitting into said annular indentation of said sealing plug, the end of said first cylindrical section being pressed tightly against said first annular shoulder in said proximal port, said first cylindrical section being caused to expand radially against said first coaxial recess; whereby said sealing plug forms a fluid-tight self-sealing injection port by axial and radial expansion.

11. The connector assembly according to claim 7 wherein said distal port of said first connector is integrally connected to and in fluid connection with a plurality of tubes, one of said tubes being a fluid outlet and at least one of remaining tubes being a fluid inlet.

12. The connector assembly according to claim 11, wherein said injection port on said first connector comprises; a first and a second coaxial recess forming a first annular shoulder and a second annular shoulder at said proximal port, said first coaxial recess being larger than the fluid passage, and said second coaxial recess following said first coaxial recess and being larger than said first coaxial recess; and,     a resilient elastomeric sealing plug constructed to tightly fit said proximal port, said sealing plug being formed with a first cylindrical section formed by a second larger cylindrical section, said first cylindrical section having a smaller cross-section than said second cylindrical section; a coaxial cylindrical blind hole opening in said first cylindrical section, and an annular indentation being formed around the periphery of the end of said second cylindrical section; said sealing plug being pressed in said proximal port with said larger cylindrical section having a tight fit with said second coaxial recess, the end portion of said proximal port being bent inwardly to form an annular lip, said annular lip fitting into said annular indentation of said sealing plug, the end of said first cylindrical section being pressed tightly against said first annular shoulder in said proximal port, said first cylindrical section being caused to expand radially against said first coaxial recess; whereby said sealing plug forms a fluid-tight self-sealing injection port by axial and radial expansion.

13. An injection port connector comprising;

a tubular body having a coaxial fluid passage therethrough from a distal port to a proximal port;

said tubular body having an annular recess around the outside thereof adjacent said proximal port;

lug shaped locking means integrally formed with a band, said band being deformable to fit into said annular recess on the outside of said tubular body;

a first and a second coaxial recess forming a first annular shoulder and a second annular shoulder at said proximal port, said first coaxial recess being larger than the fluid passage, and said second coaxial recess following said first coaxial recess and being larger than said first coaxial recess; and     a resilient elastomeric sealing plug constructed to tightly fit said proximal port, said sealing plug begin formed with a first cylindrical section joined by a second larger cylindrical section, said first cylindrical section having a smaller cross-section than said second cylindrical section; a coaxial cylindrical blind hole opening in said first cylindrical section, and an annular indentation being formed around the periphery of the end of said second cylindrical section; said sealing plug being pressed in said proximal port with said larger cylindrical section having a tight fit with said second coaxial recess, the end portion of said proximal port being bent inwardly to form an annular lip, said annular lip fitting into said annular indentation of said sealing plug, the end of said first cylindrical section being pressed tightly against said first annular shoulder in said proximal port, said first cylindrical section being caused to expand radially against said first coaxial recess;

whereby said sealing plug forms a fluid-tight self-sealing injection port by axial and radial expansion and said lugshaped locking means is rotatable relative to but not removable from said tubular body.

\* \* \* \* \*